(12) United States Patent
Kwan et al.

(10) Patent No.: US 10,441,529 B2
(45) Date of Patent: Oct. 15, 2019

(54) CAVITATION-INDUCING POLYMERIC NANOPARTICLES

(71) Applicant: Oxsonics Limited, Oxford (GB)

(72) Inventors: James Kwan, Oxford (GB); Rachel Myers, Oxford (GB); Constantin-Cassios Coussios, Oxford (GB); Apurva Shah, Oxford (GB)

(73) Assignee: Oxsonics Limited, Oxford (GB)

( * ) Notice: Subject to any disclaimer, the term of this patent is extended or adjusted under 35 U.S.C. 154(b) by 87 days.

(21) Appl. No.: 15/037,664

(22) PCT Filed: Nov. 19, 2014

(86) PCT No.: PCT/GB2014/053416
§ 371 (c)(1),
(2) Date: May 18, 2016

(87) PCT Pub. No.: WO2015/075442
PCT Pub. Date: May 28, 2015

(65) Prior Publication Data
US 2016/0296465 A1    Oct. 13, 2016

(30) Foreign Application Priority Data

Nov. 19, 2013    (GB) .................................. 1320413.6

(51) Int. Cl.
| | |
|---|---|
| *A61K 9/00* | (2006.01) |
| *A61K 9/51* | (2006.01) |
| *A61B 8/08* | (2006.01) |
| *A61M 37/00* | (2006.01) |
| *C08L 25/06* | (2006.01) |
| *A61K 49/22* | (2006.01) |

(52) U.S. Cl.
CPC .......... *A61K 9/0009* (2013.01); *A61B 8/0841* (2013.01); *A61K 9/5138* (2013.01); *A61K 49/223* (2013.01); *A61M 37/0092* (2013.01); *C08L 25/06* (2013.01); *C08L 2203/02* (2013.01)

(58) Field of Classification Search
CPC .. A61K 9/0009; A61K 9/5138; A61K 49/223; A61B 8/0841; A61M 37/0092; C08L 25/06; C08L 2203/02
See application file for complete search history.

(56) References Cited

U.S. PATENT DOCUMENTS

| | | | |
|---|---|---|---|
| 2009/0041833 A1* | 2/2009 | Bettinger | ............. A61K 9/0009 424/450 |
| 2010/0178305 A1 | 7/2010 | Rapoport | |
| 2011/0064810 A1 | 3/2011 | Ghanavi | |
| 2011/0177005 A1 | 7/2011 | Rapoport et al. | |
| 2016/0250352 A1 | 9/2016 | Mo et al. | |
| 2016/0263222 A1 | 9/2016 | Mo et al. | |

FOREIGN PATENT DOCUMENTS

| | | |
|---|---|---|
| WO | 2010/052494 | 5/2010 |
| WO | 2010/105058 | 9/2010 |
| WO | 2011/036475 | 3/2011 |
| WO | 2011/069082 | 6/2011 |
| WO | 2012/066334 | 5/2012 |
| WO | 2012/094541 | 7/2012 |
| WO | 2013/055791 | 4/2013 |
| WO | 2015/059459 | 4/2015 |
| WO | 2015/059460 | 4/2015 |

OTHER PUBLICATIONS

Sarah J. Wagstaffe, Heiko A. Schiffter, Manish Arora, and Constantin-C. Coussios, "Sonosensitive nanoparticles for controlled instigation of cavitation and drug delivery by ultrasound", American Institute of Physics Conference Proceedings, 1481, 426-431 (2012).*
Hui Lv, Quan Lin, Kai Zhang, Kui Yu, Tongjie Yao, Xuehai Zhang, Junhu Zhang, and Bai Yang, "Facile Fabrication of Monodisperse Polymer Hollow Spheres", Langmuir 2008, 24, 13736-13741.*
Jian Ye, Pol Van Dorpe, Willem Van Roy, Gustaaf Borghs, and Guido Maes, "Fabrication, Characterization, and Optical Properties of Gold Nanobowl Submonolayer Structures", Langmuir 2009, 25, 1822-1827.*
International Search Report corresponding to PCT/GB2014/053416 dated Mar. 26, 2015; 2 pages.
Apfel, R. E. and C. K. Holland, "Gauging the likelihood of cavitation from shortpulse, low-duty cycle diagnostic ultrasound," *Ultrasound in Medicine and Biology*, vol. 17, pp. 179-185 (1991).
Bremond, N. et al., "Controlled multibubble surface cavitation," *Physical Review Letters*, vol. 96, Jun. 2006.
Bryaskova et al, "Synthesis of poly(vinyl acetate)-b-polystyrene and poly(vinyl alcohol)-b-polystyrene copolymers by cobalt-mediated radical polymerization," *Journal of Polymer Science*, Part A: Polymer Chemistry, vol. 45, No. 1, 2007, pp. 81-89.
Deotare et al, "Fabrication of silica nanocomposite-cups using electrospraying", *Nanotechnology*, vol. 17, No. 5, 2006, pp. 1380-1383.
European Medicines Agency: "SonoVue—EPAR summary for the public", Nov. 7, 2007 (Nov. 7, 2007), pp. 1-3, XP055176303.
Graham, S. et al., "Inertial cavitation to non-invasively trigger and monitor intratumoral release of drug from intravenously delivered liposomes," *Journal of Controlled Release*, vol. 178, pp. 101-107 (2014).
Kwan et al., Inertial cavitation at the nanoscale; Proceeding of Meetings on Acoustics, vol. 19, 075031 (2013).

(Continued)

*Primary Examiner* — John Pak
*Assistant Examiner* — Nathan W Schlientz
(74) *Attorney, Agent, or Firm* — Kilpatrick Townsend & Stockton LLP (57) ABSTRACT

The invention disclosed herein relates to a nanoparticle comprising: a cup having a cavity, and a gas pocket present in the cavity, wherein the gas pocket is partially encapsulated by the cup. Typical uses of the nanocups include initiating inertial cavitation during simultaneous exposure to ultrasound, and/or as drug carriers to achieve targeted drug delivery in response to ultrasound excitation.

34 Claims, 8 Drawing Sheets

(56) References Cited

OTHER PUBLICATIONS

Liu et al, "Morphology-controllable fabrication of ordered platinum nanoshells with reduced symmetry," *Nanotechnology*, vol. 17, No. 16, 2006, pp. 4191-4194.

Stride, E. P. and C. C. Coussios, "Cavitation and contrast: the use of bubbles in ultrasound imaging and therapy," *Proceedings of the Institution of Mechanical Engineers Part H-Journal of Engineering in Medicine*, vol. 224, pp. 171-191 (2010).

Okubo, M. et al., "Formation mechanism of micron-sized monodispersed polymer particles having a hollow structure," *Colloid Polym Sci* 275:992-997 (1997).

Omi, Shinzo et al., "Study of particle growth by seed emulsion polymerization with counter-charged monomer and initiator system," *Colloids Surfaces A: Physiochem. Eng. Aspects* 153 (1999) 165-172.

Arshady, R., "Suspension, emulsion, and dispersion polymerization: A methodological survey," *Colloid & Polymer Sci.* 270:717-732 (1992).

Fujibayashi, Teruhisa and Masayoshi Okubo, "Preparation and Thermodynamic Stability of Micron-Sized, Monodisperse Composite Polymer Particles of Disc-like Shapes by Seeded Dispersion Polymerization," *Langmuir* 23:7958-7962 (2007).

Xu, Jiangping et al., "The generation of polymeric nano-bowls through 3D confined assembly and disassembly," *Soft Matter* 12:3683-3687 (2016).

\* cited by examiner

CAVITATION-INDUCING POLYMERIC NANOPARTICLES

CROSS-REFERENCE TO RELATED APPLICATIONS

This application is a national phase application under 35 U.S.C. 371 claiming priority to PCT/GB2014/053416, filed Nov. 19, 2014, which application claims the benefit of priority to GB 1320413.6, filed Nov. 19, 2013, the teachings of which are hereby incorporated by reference in their entireties for all purposes.

The invention disclosed herein relates to the field of biomedical acoustics, and in particular nanoscale initiators of inertial cavitation and their utility in therapeutic and diagnostic methods.

A limited number of cavitation agents are known, and include micron-sized gas encapsulated within a lipid, protein or polymer coating (microbubbles). A microbubble expands during the negative pressure cycle of an applied acoustic wave such as an ultrasound wave. If the negative pressure amplitude is sufficiently large for a particular bubble size, the bubble undergoes unstable growth during the negative pressure cycle, subsequently collapsing during the positive pressure cycle of the wave. The nearly instantaneous collapse under the effect of the inertia of the surrounding liquid generates mechanical shockwaves, and is typically associated with broadband acoustic emissions. This process of inertial cavitation has been shown to be useful in a variety of biomedical and non-biomedical applications. Biomedical applications include histotripsy, thermal ablation, targeting and enhancement of drug delivery, sonothrombolysis and diagnostic ultrasound imaging. Non-biomedical applications include sonochemistry, sonofusion, water treatment and the use of ultrasound to characterize material properties, such as those disclosed in WO 2011/036475.

Achieving inertial cavitation in a pure liquid requires very large pressure amplitudes, typically in the order of GPa, capable of overcoming the tensile strength of the liquid. Introducing pre-existing void spaces into the liquid will significantly lower the pressure amplitude required to initiate inertial cavitation (also known as the inertial cavitation threshold). This threshold is dependent upon the ultrasound excitation frequency, the bubble size and surrounding liquid properties (R. E. Apfel and C. K. Holland, "GAUGING THE LIKELIHOOD OF CAVITATION FROM SHORT-PULSE, LOW-DUTY CYCLE DIAGNOSTIC ULTRASOUND," *Ultrasound in Medicine and Biology*, vol. 17, pp. 179-185, 1991): this means that, in a given liquid excited at a given frequency, the cavity size is the most important determinant of the inertial cavitation threshold.

Free bubbles are typically not used as cavitation nucleation agents owing to their rapid dissolution. Therefore, surface-active stabilizers have been used to increase the lifetime of the bubble. Several agents have thus been previously proposed as potential cavitation nuclei, which can be artificially introduced into the medium in order to lower the inertial cavitation threshold. The most commonly used agents are microbubbles stabilized by a surfactant (such as a lipid or protein shell), typically encapsulating a gas that has low solubility in the surrounding medium. Solid particles capable of entrapping gas on surface crevices or inclusions have also been described as potential cavitation nucleation agents.

Both microbubbles and solid particles are typically at least several microns in size. However, there are many applications that require sub-micron cavitation nuclei or nuclei that do not exhibit significant buoyancy or sedimentation characteristics. For example, achieving uniform cavitation in a liquid would require an agent that can remain in suspension for extended periods of time, which is not possible with either buoyant microbubbles or sinking microparticles. In the biomedical field, for instance, blood vessels are typically no smaller than 8 microns in diameter, but the tight junctions between endothelial cells lining the vessel wall are smaller than 100 nm in healthy tissue and between 100-800 nm in diseased or cancerous tissue. Therefore microbubbles are confined to the blood vessels, and are incapable of extravasating into the perivascular space and subsequent tissue layers. This is particularly limiting in therapeutic applications, such as drug delivery, seeking to treat tissue that is remote from blood vessels.

Nanoscale cavitation agents have thus been proposed to address these limitations. These include nanodroplets (US20100178305, US20110177005), polymeric nanobubbles (WO 2013 055791), and layer-by-layer bead constructs that entrap surface nanobubbles, such as those disclosed in WO 2012/066334 and Kwan et al., Proceedings of Meetings on Accoustics, vol. 19, 075031 (2013).

While it is possible to control the overall size of such known nanoscale cavitation agents, the size of the gas voids present in such agents can be difficult to predict and control for a variety of reasons. Nanodroplets are designed to vaporize upon lowering of the ambient pressure, such as that caused by an ultrasound wave. As a result, they are essentially vapour bubbles, which collapse with greater difficulty than gas bubbles. They also tend to agglomerate post-injection and are highly susceptible to temperature fluctuations, meaning that the nature and size of cavitation nuclei can neither be known nor controlled. Polymeric nanobubbles are stabilized with a rigid thin shell fully surrounding the nanobubble, which must rupture before inertial cavitation can occur, resulting in elevated inertial cavitation thresholds. Layer-by-layer solid nanoparticles are challenging to manufacture reliably, and even though the overall particle size can be tuned, the size of the gas voids cannot be directly controlled.

Accordingly there exists a need to provide a nanoscale cavitation initiator that can be readily manufactured, in which the size of the gas void can be varied as per the requirements and tightly controlled, resulting in a significant lowering of the inertial cavitation threshold.

The present invention provides a nanoparticle, which is acoustically tuneable. The nanoparticle comprises a gas pocket that is partially encapsulated in a cup-shaped surrounding. The nanoparticle is capable of reducing inertial cavitation thresholds to clinically relevant levels by stabilising a nanoscopic pocket of gas while still allowing it to expand as part of the cavitation process, features which would not be seen if existing microbubble technology were simply scaled down to the nanoscale. Further, the size of the cup's cavity, and therefore the size of the nanobubble, can be accurately controlled to produce a nanoscale cavitation initiator tuned to respond to unique acoustic settings.

Thus, the present invention provides a nanoparticle comprising:

a cup having a cavity, and a gas pocket present in the cavity, wherein the gas pocket is partially encapsulated by the cup.

Typically, the nanoparticle comprises a single cup and correspondingly a single gas pocket. Thus, the nanoparticle is typically an individual nanocup rather than an array of nanocups or an agglomerate of multiple nanocups. Nanoparticles having a single cup provide a greater degree of control over the cavity size, and accordingly over the cavitation effect achieved. Thus, single cup nanoparticles provide greater predictability of response when cavitation is induced by ultrasound. The nanoparticle is in one embodiment a nanoparticle in the form of a cup having a cavity, wherein a gas pocket is present in the cavity, the gas pocket being partially encapsulated by the cup.

The present invention also provides a method of producing the cup-shaped nanoparticles comprising:
  providing a seed particle;
  partially coating the seed particle, typically by carrying out polymerisation on the surface of the seed particle, to provide a cup having a cavity;
  drying the cup; and
  providing gas to the cup to produce a pocket of the gas within the cavity, the last two steps typically being carried out by drying the cup in an appropriate gas, e.g. in air.

The process enables the size of the gas pocket to be accurately controlled by use of an appropriately sized seed particle and therefore provides a reliable and repeatable technique for producing the nanoparticles of the invention.

In certain embodiments of the invention, the nanoparticles act as drug delivery vehicles. This embodiment allows both targeting of the therapeutic, and, importantly, triggered "on-demand" release of the therapeutic in response to stimulus.

Achieving release of therapeutic agents from nanoparticles triggered by an external stimulus is a major challenge. A particular application of this is drug delivery to tumours, whereby achieving delivery of a therapeutically relevant concentration of the drug in the tumour region beyond the vasculature is key to therapeutic efficacy. Ultrasound is particularly well suited as an external stimulus for triggered release because it can readily propagate to distances ranging from tens of cm in the MHz range to several meters in the kHz range. Several approaches have been proposed for ultrasound-triggered drug release. Typically, these methods take advantage of the enhanced permeation and retention (EPR) effect wherein particles between 100-400 nm accumulate in the cancerous mass. Thus, ultrasound-triggered drug delivery utilise nanoparticles small enough to accumulate in tumours that are sensitive to thermal and/or mechanical changes in the ambient medium. For example, thermo-sensitive liposomes will release their payload at temperatures above 42° C., but require high amounts of energy delivered to the patient. Alternatively, sonosensitive liposomes release the drug in the presence of mechanical disruption due to inertial cavitation. Unfortunately, the delocalisation of cavitation nuclei, which are constrained to the vasculature, and the liposomes that are situated in the tumour limit the efficacy of this delivery scheme. Instead, nanodroplets have been proposed as a cavitation nuclei that will accumulate within the tumour. However, these particles are inherently unstable due to the droplet residing in a metastable thermodynamic state. Ultimately, these particles are highly sensitive to thermal fluctuations, resulting in pre-site vaporisation and coalescence.

Accordingly, solutions available have not provided the desired nanoparticle capable of achieving triggered release 'on-demand' in response to low energy ultrasound excitation. The present invention, however, provides such triggered release by providing a drug, which is released from the nanoparticle on cavitation.

Thus, the present invention provides a nanoparticle of the invention which comprises a release agent, where the release agent is separated from the nanoparticle on cavitation. The release agent is typically a drug, for example a therapeutic, or a diagnostic material.

In some embodiments, the release agent is provided as a drug layer that is present in the cavity, typically, for example, coating the inner surface of the cup. In such embodiments, the gas pocket will act as a "plug", protecting the drug from instantly releasing upon exposure to water or plasma and thereby reducing non-specific systemic effects on healthy tissue. When cavitation of the gas pocket is induced, for example by applying ultrasound, the cavity can be "unplugged" and the drug can be released. Alternatively, a drug can be incorporated within the structure of the cup, e.g. within a polymeric cup, or coated to the outer surface of the cup, for faster release of therapeutic drugs when exposed to ultrasound. Because cavitation can be induced locally, e.g. by applying ultrasound in the region of the drug's physiological target, in these embodiments, the nanoparticles can be used in a method of targeted drug delivery.

The present invention also provides a nanoparticle as described herein for use in a method of treatment or diagnosis of a human or animal subject, wherein the method comprises inducing cavitation in the subject, e.g. by exposing the subject to ultrasound.

The present invention also provides a method of treatment or diagnosis of a human or animal subject, wherein the method comprises administering a nanoparticle as described herein and inducing cavitation in the subject, e.g. by exposing the subject to ultrasound.

The present invention also provides use of a nanoparticle as described herein in the manufacture of a medicament for treatment or diagnosis of a human or animal subject, wherein said treatment or diagnosis comprises inducing cavitation in the subject, e.g. by exposing the subject to ultrasound.

The present invention also provides a composition comprising a plurality of nanoparticles as described herein and optionally a carrier or diluent, typically a pharmaceutically acceptable carrier or diluent, e.g. a liquid medium. In some embodiments the nanoparticles in the composition are substantially monodisperse. They may for example have a polydispersity index (PDI) of 0.20 or less, e.g. 0.19 or less, 0.18 or less, 0.17 or less, 0.16 or less, or 0.15 or less. The liquid medium may be aqueous in nature.

BRIEF DESCRIPTION OF THE DRAWINGS

FIG. 7a shows the particle size of small, medium and large nanocups according to the invention, whilst FIG. 7b shows the cavity size of the same nanocups. FIGS. 7c and d show the caviation thresholds of these nanocups.

FIG. 8d shows the cavitation effect of the nanocups of the invention at higher amplitude ultrasound.

NANOCUPS

As used herein a nanoparticle is any particle having a size of from 1 nm to 1000 nm. The size of the nanoparticle is typically the mean diameter of the nanoparticle (s in FIG. 1). The diameter is typically determined by electron microscopy. Where a plurality of nanocups are present in a composition, the cumulant average is typically taken as the size of the nanoparticles. This can be determined by dynamic light scattering.

As used herein the term "part-spherical" describes a shape that forms part of a sphere. The term "part-spherical" includes shapes such as a spherical cap, a hemisphere, and a sphere having its top truncated above its equator (i.e. the part of a sphere complementary to a spherical cap). Substantially part-spherical includes shapes such as those forming parts of a spheroid, and parts of a sphere or spheroid having irregularities such as depressions and protrusions.

Cups which are not part-spherical can be used in the nanoparticle of the present invention, and any cup-shape can be used, i.e., a shape having a cavity that is capable of partially encapsulating a gas pocket. Shallow or small indentations/imperfections on the surface of a nanoparticle, for example those having a depth of less than about 5 nm, typically less than about 10 nm or less than about 20 nm, and/or having an opening of less than about 5 nm, typically less than about 10 nm, or less than about 20 nm, are not generally capable of encapsulating a gas pocket and are not therefore considered cavities as used herein. Thus, a nanoparticle having a single cavity may also comprise such small/shallow imperfections or indentations on its surface.

As used herein the gas pocket partially encapsulated by the cup is typically a gas pocket having a part of its surface which is encapsulated by the cup, optionally with one or more layers present between the cup and the gas pocket, and a part of its surface which is not encapsulated by the cup and may be exposed to a medium in which the nanoparticle may be present, e.g., a liquid medium.

As used herein the size of the opening of a cavity is the maximum dimension of the cavity measured at the rim of the cup (p in FIG. 1), typically the part of the cup that forms a boundary between the encapsulated part of the gas pocket and the un-encapsulated part of the gas pocket. In the case of a substantially part-spherical cavity, the opening will be substantially circular and the size is measured as the diameter of the opening. The size of the opening of a cavity can be determined by transmission electron microscopy.

Figure 1:
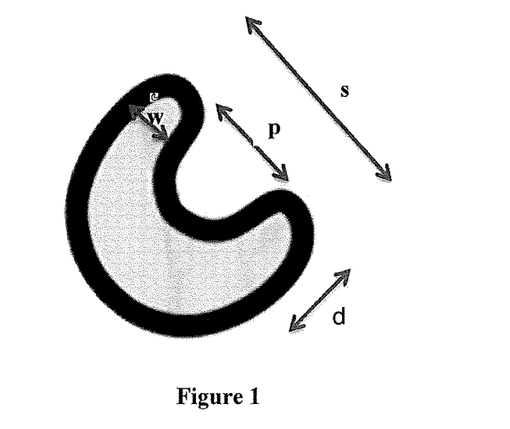
FIG. 1 depicts a typical nanocup according to the invention.

As used herein the wall thickness of the cup refers to the shortest distance from a point on the surface of the cup facing the cavity, through the cup, to a point on the opposite surface of the cup (w in FIG. 1). The wall thickness of a cup can be determined by transmission electron microscopy.

As used herein, the depth of the cup refers to the maximum distance from the level of the rim of the cup to the base of the cup (d in FIG. 1). The depth of the cup can be determined by transmission electron microscopy.

In some embodiments the thickness may vary within a cup, or from cup to cup in a composition comprising a plurality of cups, in which case an average can be determined. In some embodiments the thickness may be uniform, or substantially uniform, within a cup or from cup to cup in a composition comprising a plurality of cups.

As used herein the term "substantially uniform thickness" relates to a shape with a maximum thickness that is no more than 25% greater than its minimum thickness, e.g., no more than 20% greater, no more than 15% greater, no more than 10% greater or no more than 5% greater.

The nanoparticle of the present invention typically has a size (s) of at least 60 nm or at least 100 nm and up to 1000 nm, e.g. up to 500 nm or up to 300 nm. For example, the nanoparticle may have a size of from 60 to 500 nm or from 100 to 300 nm.

In embodiments where the nanoparticle is for use in a method of treating a tumour, then a particular size of the nanoparticle may be desired in order to improve accumulation in tumour tissue by the enhanced permeability and retention (EPR) effect. Tumour tissues may contain neovasculature having abnormal form and architecture, leading to abnormal molecular and fluid transport dynamics. That can cause nanoparticles of around 100 to 500 nm, e.g. 100 to 300 nm in size to accumulate in tumour tissue much more than they do in normal tissues. Nanoparticle sizes of 100 to 500 nm, e.g. 100 to 300 nm may therefore be desired, in particular for use in methods of treating a tumour.

The desired size and shape of the cavity containing the gas pocket is determined by the ultrasound frequency to be used, typically in the range 0.5 MHz to 5.0 MHz, in order to minimize the rarefactional pressure amplitude required to initiate inertial cavitation. Ultrasound pressure amplitudes less than 5 MPa are preferred, e.g. 3 MPa or less, 2.5 MPa or less, or 2 MPa or less. Ultrasound pressure amplitudes as low as 0.5 MPa can yield extensive inertial cavitation at frequencies as high as 2 MHz in the presence of the nanocups.

The cavity is typically substantially part-spherical, e.g. substantially hemispherical or hemispherical. The cavity typically has an opening size (p), for a substantially part-spherical cavity a diameter at the opening, of from 50 to 900 nm, e.g. at least 50 nm, 100 nm or at least 200 nm and no more than 700 nm, 600 nm, or no more than 400 nm. The cavity may, for example, be from 50 to 400 nm or 100 to 600 nm. A skilled person will be able to select an appropriate cavity shape and size to complement desired ultrasound parameters, and produce nanoparticles having the desired cavity shapes and sizes based on the methods disclosed herein for producing the nanoparticles.

The ratio of the size of the opening to the size of the nanoparticle (ratio p:s in FIG. 1) is typically from 1:3 to 5:6, for example from 1:2 to 2:3.

The cavity typically has a depth of more than 30 nm, preferably more than 50 nm. For example, the cavity typically has a depth of from 60 to 500 nm, for example from 80 to 400 nm.

Cavities having a larger size (e.g. a depth of greater than 30 nm, preferably greater than 50 nm or more; and/or an opening of 50 nm or more) have the advantage that greater cavitation effects can be caused.

The wall thickness (w) of the cup is typically 10 to 100 nm, e.g. 30 to 70 nm or about 50 nm. The wall thickness of the cup can be selected and accurately controlled based on the methods disclosed herein for producing the nanoparticles. The wall thickness of the cup is typically substantially uniform, both within a single nanoparticle and from one nanoparticle of the compositions of the present invention to another. The wall thickness is typically a fixed proportion of the overall cup size.

The cup is typically formed of a polymeric material, but could also be formed from any solid material that can be formed into a nanocup. Thus, the cup typically comprises a polymer, preferably it consists essentially of a polymer.

For example, the cup may be formed of a polymer capable of being formed in an emulsion polymerisation procedure. Suitable polymers include poly(methyl methacrylate) (PMMA), poly(2-hydroxyethyl methacrylate) (pHEMA), copolymers such as poly(lactic-co-glycolic) acid (PLGA), polystyrene and divinylbenzene, and methyl methacrylate/ 2-hydroxyethyl methacrylate copolymer, and pH or temperature responsive polymers such as poly(N-isopropylacrylamide) (PNIPAM). Other suitable polymers include, but are not limited to, polymers classed as polyanhydrides.

pH- or temperature-responsive polymers such as PNIPAM can be used to enhance the release of a drug encapsulated within the nanocup and/or the uptake of that drug at its target e.g. a tumour. pH-responsive polymers may be preferred in the context of tumour therapy, as the pH may be lower in a tumour than in healthy tissue (e.g. in hypoxic regions which are distal to blood vessels). Temperature-responsive polymers may be preferred for use alongside hyperthermia or ablative treatments, such as High Intensity Focussed Ultrasound (HIFU), microwaves, radio-frequency (RF) or lasers.

In some embodiments the cup is formed of a cross linked polymer. Cross linking of the polymer can be achieved by introducing a cross linking agent into the monomer mixture prior to or during polymerisation. Suitable cross linking agents include divinylbenzene (DVB) or vinylsilane. Cross linking can also be present in the polymer in the form of regions of disulphide bonds. Regions of disulfide bonds can be introduced using thiol chemistry. A cross linked polymer may be used to provide rigidity to the nanoparticle. Rigidity may be desired for example to reduce or prevent shattering of the cup during cavitation. Degree of cross linking may be determined by various spectrographic methods, such as Raman spectroscopy or nuclear magnetic resonance spectroscopy, or polymer swelling techniques.

A polymeric cup may comprise a polymer formed from two or more, for example two or three, different monomer units. The polymer may be produced by copolymerising a mixture of the monomers, and/or by providing one or more pre-polymers which are linked by co-polymerisation, or via cross-linking agents.

The cup is typically biocompatible, i.e. capable of performing its desired function with respect to a medical therapy or method of diagnosis without eliciting any therapeutically unacceptable local or systemic effects in the recipient or beneficiary of that therapy or diagnosis.

The gas present in the gas pocket is not particularly limited but is typically air, nitrogen, oxygen, a perfluorocarbon such as perfluoropropane, or a mixture thereof.

The gas pocket may be the same size and shape as the cavity. For example, if the cavity is a hemisphere with a diameter d at its opening, then the gas pocket may be a hemisphere of diameter d. Alternatively, the gas pocket may be larger than the cavity, i.e. it may protrude from the rim of the cup. It may protrude from the rim of the cup a distance that is 10% or more of the depth of the cup, e.g. 20% or more, 50% or more 80% or more or 100% or more. The depth of the cup and the degree to which the gas pocket may protrude can be determined using transmission electron microscopy. In some embodiments the cavity is part-spherical or substantially part-spherical with a curvature of radius r, and the gas pocket is a sphere with radius r. In an example of this embodiment the cavity is a hemisphere with a diameter d at its opening, and the gas pocket is a sphere of radius ½ d.

A particular advantage of the nanocups of the invention is that the cavity size may be controlled in order to provide tuneable cavitation initiators. The nanocups of the invention therefore typically have a cavity opening size which is predictable and repeatable. Such nanocups having predictable cavity opening size are therefore tuneable nanocups.

Process for Producing Nanocups

The nanoparticles can be produced by forming a cup by a seeded emulsion polymerisation technique, optionally forming a drug layer in the cavity of the cup, and drying the cup in the presence of a gas to introduce the gas pocket.

The size and shape of the cavity can be selected and accurately controlled by selecting the seed particles to be used. Thus, the seeded emulsion polymerisation technique typically uses a seed particle having a size and shape complementary with the desired size and shape of the cavity. For example, a spherical seed particle can be used to produce a cup having a part-spherical cavity. Using larger seed particles can form a larger cavity, and similarly, using smaller seed particles can produce a smaller cavity. Seed particles used will typically have a size of 50 to 900 nm, e.g. at least 50 or at least 100 nm and up to 600 nm, up to 400 nm or up to 300 nm.

Emulsion polymerisation is typically carried out by mixing seed particles, monomers, and optionally a cross linking agent in a suitable medium such as water, mixing to produce turbulent conditions and adding a suitable initiator such as potassium persulfate. The emulsion polymerisation reaction is allowed to continue at a suitable temperature for a suitable period of time. A skilled person will be able to select appropriate temperature and time parameters for the particular reaction mixture used, but the polymerisation typically takes place over 4-6 hours at a temperature of 70 to 90° C., e.g. for about 5 hours at about 80° C.

The polymerisation is typically a free radical polymerisation process. The polymers coated onto the seed particle may be solid or liquid polymers that co-polymerise with the seed particle.

Where the cup is formed from two or more monomer units, the different monomers may be provided to the emulsion polymerisation at the beginning of polymerisation, or alternatively one or more monomers may be provided part way through the polymerisation process. Alternatively, one or more of the monomer units may be pre-polymerised and a pre-polymer provided to the polymerisation mixture, either at the beginning of polymerisation or part way through polymerisation. Typically, one or more of the monomers or pre-polymers may have a greater affinity for the seed particle. Thus, the polymerisation may provide a cup having one monomer unit predominantly formed on the inner surface of the cup (i.e. the monomer having greatest affinity for the seed particle) and a different monomer unit predominantly on the exterior surface of the cup. This may provide a cup having differing surface properties on the interior and exterior surfaces.

In the case of polymeric nanocups, the seed particle typically remains chemically bound to the inner surface of the nanocup, the seed particle material typically being itself incorporated into the cup. In the case of a complete reaction of all available seed particles, there will therefore be no seed particles remaining that need to be removed. Large agglomerates and small byproducts are removed through centrifugation and filtration. The final shape, size and successful formation of the nanocups can be verified by transmission electron microscopy (TEM) acquired at multiple tilt angles of the grid plane, that can be reconstructed into a 3D model, as shown in the inset image of FIG. 2.

The wall thickness of the cup can be controlled by selecting the amount of the monomer mixture relative to the amount of seed particles present in the reaction mixture. Raising the amount of monomer relative to the number of seed particles will increase the wall thickness of the resulting cups, and reducing the amount of monomer relative to the number of seed particles will reduce the wall thickness of the resulting cups. Additionally, the wall thickness of the cup can be adjusted by modulating the duration the polymerisation takes place, i.e., longer reaction times result in thicker cups provided that there is enough reactant.

After emulsion polymerisation has been carried out, the product can be washed, e.g., by centrifuging, in order to remove any excess polymer. After washing the product is typically suspended in a suitable medium such as water before drying.

The product can be dried by any suitable technique such as freeze-drying or air-drying. If freeze-dried a cryoprotectant is not typically used. Air-drying is preferred and may be carried out at elevated temperatures, for example, or in a desiccator. Air-drying may be carried out over a period of 12-36 hours, e.g., 24 hours. In one embodiment, air drying is carried out at a temperature of 40 to 50° C. for 6 to 18 hours, e.g., about 12 hours and then in a desiccator for 15 hours at 18-24° C.

If dried in air the gas pocket in the nanoparticles of the invention will be air gas pockets. Alternative gasses can be used for the gas pocket by carrying out the drying step in the desired gas. For example, drying can be carried out in air, and the resulting nanoparticles having an air gas pocket can be subjected to a vacuum to remove the air gas pocket, and contacted with the desired gas to introduce a new gas pocket of the desired gas. Drying the nanocups in a gaseous atmosphere provides the required gas pocket within the cavity of the cup. Prior to drying, no gas pocket is present.

The dried nanocups may be resuspended in a liquid medium such as an aqueous solution. Suitable solutions include dilute glucose solution, e.g. 0.5-10%, preferably 1-8%, e.g. about 5% glucose solution. Typically, the solution is then mixed to maximise particle dispersion. Dried nanocups retain their gas pocket on resuspension. Thus, nanocups which have been dried in a gaseous atmosphere and resuspended differ from those formed directly in solution, in that a gas pocket is present in the cavity, due to the drying step.

Following resuspension of the nanocups, the solution is preferably filtered to remove agglomerated material. Syringe filtration, for example at 1-5 µm, typically 1.5-3 µm, may be used to remove fine particles. This limits the particles present to those having a nanoparticle size of less than the filtration limit. A combination of coarse filtration followed by syringe filtration may be used.

Where nanocups in dried form are desired, for example for ease of transportation, the resuspension and filtration steps can be omitted. Dried nanocups are typically resuspended and, depending on the resulting size distribution, the suspension optionally filtered, prior to use.

Figure 6:
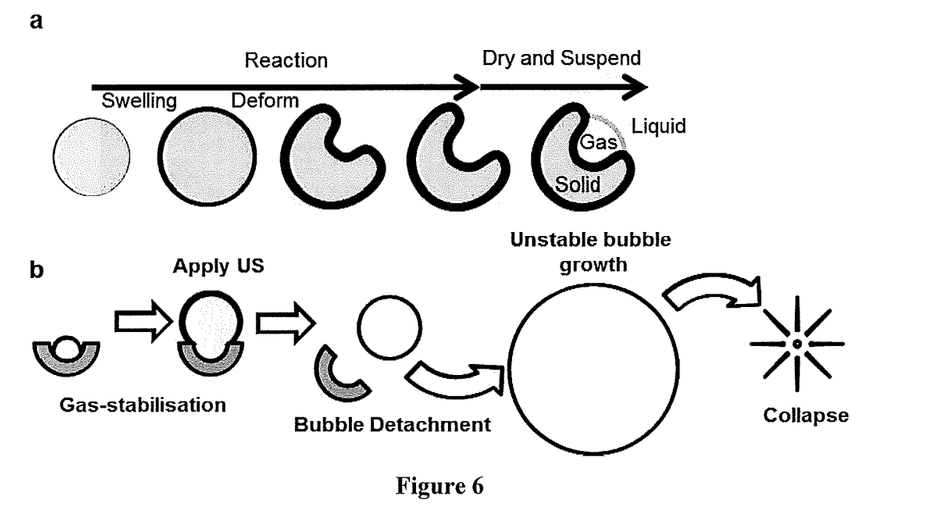
FIG. 6 depicts schematically the process for producing nanocups according to the invention.

FIG. 6 schematically depicts the process of producing the nanocups according to the invention. FIG. 6a) shows individual template particles which were coated with a copolymer, which induced swelling and deformation of the spherical particle. The resulting nanocup was dried and suspended to entrap gas in the cavity. FIG. 6b) gives a diagrammatic representation of the proposed mechanism for inertial cavitation for nanoparticle systems. Initially the bubble is stabilized within the cavity. With enough negative pressure, the bubble can extend onto the mouth of the cavity, and eventually detach from the particle. For inertial cavitation to occur, the detached bubble must grow unstably before finally collapsing under the inertia of the surrounding medium.

Nanocups as Drug Delivery Vehicles

The nanoparticles of the invention may be used as drug delivery vehicles by incorporating a release agent, typically a drug, for example either within the cavity, within the cup, or on the exterior surface of the cup. The release agent may form a layer which is typically on the exterior surface of the cup, in the cup or on the interior surface of the cup, within the cavity. A release agent as referred to herein is a material that is released from the nanoparticle on cavitation. Typically, the release agent is a drug, i.e. a therapeutic or diagnostic, for example a pharmaceutical or biological material. Typically, the release agent is a material that is useful in therapy or diagnosis of a human or animal subject. The description herein refers to a drug or a drug layer being present in the nanoparticle. However, it should be understood that alternative materials, which are usefully released on cavitation, for example when used in non-medical applications, may also be used as the release agent. Any reference to a drug or drug layer therefore is also envisaged as being replaced by an alternative release agent or release agent layer where appropriate.

In embodiments where a drug layer is present in the cavity or within the cup, the nature of the drug is not particularly limited and any drug that may be useful in a method of therapy may be used. Hydrophilic drugs are preferred. Certain drugs include, but are not limited to, anticancer drugs such as doxorubicin, paclitaxel, cisplatin, gemcitabine, daunorubicin, and oxiloplatin, thrombolytic agents such as recombinant tissue plasminogen activator (rt-PA), anti-inflammatories such as acetylsalicylic acid, ibuprofen, salsalate, or antibiotic agents such as geldanamycin or penicillin. Where drugs are incorporated on the exterior of the cup, the drug is typically selected so that it can be bound to the cup in a manner which avoids dissolution on administration. Thus, the drug is released only on cavitation.

The nanoparticle may comprise two or more different drugs. For example, one drug may be provided within the cavity with a separate, different, drug being provided on the exterior surface of the cup. The two drugs are combined on release, for example on exposure to ultrasound. Thus, the nanoparticles may be used as a means to provide a combination therapy, or to provide simultaneous release of two drugs that mix only at the target site when released from the nanoparticle vehicle, e.g. following ultrasound exposure.

The addition of a drug layer can occur before formation of the cup (e.g., in the seed particle), during formation of the cup, or after formation of the cup. The timing of the incorporation of the drug layer will result in its placement on the nanocup. For example, drug laden seed particles will place the drug in the cavity of the cup. Addition of a drug during polymerisation will place the drug within the cup. The addition of drug after formation of the cup will place the drug on an exterior surface of the cup (i.e. a surface which does not face the gas pocket).

The thickness of the drug layer is dependent on the amount and location of the drug. Where the drug is incorporated into the cup itself, the thickness of the drug layer will be constrained by the wall thickness of the cup. In the case of a drug present within the cavity, the drug layer should be less than the depth of the cavity, thus enabling a gas pocket to be present at least partially encapsulated by the cavity. Controlling the thickness of the drug layer can be accomplished by modulating the duration of polymerisation and quantity of drug reactant. Drug loading is measured using drug release profiles.

Use of Nanocups

The nanoparticles of the invention can be used alone in any situation in which inertial cavitation is desired such as histotripsy, thermal ablation, sonochemistry, sonofusion and waste water treatment. For example, they can be for use in methods that involve using inertial cavitation to cause localised tissue ablation and/or removal in order to achieve a therapeutic outcome. Such methods include for example the treatment of tumours and removal of cardiac tissue in treatment of heart disease.

The nanoparticles of the invention can alternatively be used in combination with other agents, such as a drug or a diagnostic agent (e.g. an MRI contrast agent such as a Gd-based MRI contrast agent, or a fluoroscopy contrast agent). The nanoparticles of the invention can be used to deliver other agents to a target in vivo either by administering the nanoparticle and the other agent concomitantly or, in the case of a nanoparticle comprising a drug, e.g. a drug layer in the cavity of the cup, by using the nanoparticle as part of the drug formulation itself.

In the case of a separate agent being used, the nanoparticles of the invention may be administered in a single composition with the separate agent, or as a separate composition. Where two compositions are used, these may be administered simultaneously or separately. Simultaneous or substantially simultaneous administration is preferred. Application of ultrasound following administration of the nanoparticle and separate agent causes cavitation to occur. This enhances transport of the agent into cells. A particular advantage of using cavitation to enhance transport of an active agent into cells in this way is that ultrasound can be applied at selected locations, leading to the active agent being transported into cells only in those selected locations.

In one aspect of the invention, the separate agent is encapsulated in a sonosensitive liposome. Such a sonosensitive liposome can release the agent in the presence of inertial cavitation. The nanoparticles of the present invention may therefore be administered concurrently with the liposome and ultrasound applied in order to cause cavitation at the desired location, and correspondingly cause release of the active agent at the desired location.

In an alternative aspect of the invention, as discussed above, the active agent may be incorporated into the nanoparticle itself. In this case, cavitation may act to both release the agent from the nanoparticle as well as aiding transport of the active agent into cells.

When used in combination with other agents the nanoparticles can also provide real time tracking and mapping of drug distribution in vivo, for example using conventional ultrasound imaging or passive acoustic mapping of inertial cavitation (WO 2010 052494).

The ultrasound used to achieve cavitation is not particularly limited and any frequency in the range 0.5 MHz to 5.0 MHz can be used. The frequency will be matched to the tuned nanoparticles. This can lead to smaller ultrasound pressures being required to achieve cavitation. Ultrasound pressure amplitudes used are typically less than 5 MPa, e.g. 3 MPa or less.

Nanocup Compositions

The nanoparticles may be provided as a composition e.g. a pharmaceutical composition. This may be either a composition comprising a plurality of nanoparticles alone in dried form (e.g. as a powder), or a composition comprising the nanoparticles together with a pharmaceutically acceptable carrier or diluent. Typically, compositions provided together with a carrier or diluent are provided as liquid compositions comprising a suspension of nanoparticles. Said pharmaceutical composition typically contains up to 85 wt % of a nanoparticle of the invention. More typically, it contains up to 50 wt % of a nanoparticle of the invention. Preferred pharmaceutical compositions are sterile and pyrogen free.

Compositions comprising a plurality of nanoparticles in dried form are typically resuspended in a suitable liquid, e.g. an aqueous solution prior to use.

Compositions comprising a plurality of nanoparticles typically comprise nanoparticles which are substantially uniform. This has the advantage that greater control over cavitation is achieved and thus improved acoustic tuning. The preferred polydispersity index of the composition of nanoparticles is 0.2. This is typically determined by dynamic light scattering. The average particle size of a composition comprising a plurality of nanoparticles is defined herein as the modal average (i.e. the particle size displayed by the maximum number of particles). In a preferred aspect of the invention, at least 50% of the nanoparticles in the composition have a particle size within 50 nm of the average. More preferably at least 60%, 70% or 80% of the nanoparticles have a particle size within 50 nm of the average. Yet more preferably, at least 50% of the nanoparticles in the composition have a particle size within 20 nm of the average. More preferably, at least 60%, 70% or 80% of the nanoparticles have a particle size within 20 nm of the average. Dynamic light scattering may be used to determine the variation in particle size within a composition.

The average cavity size (the size of the opening of the cavity, p) of a composition comprising a plurality of nanoparticles is defined herein as the modal average (i.e. the cavity size displayed by the maximum number of particles). In a preferred aspect of the invention, at least 50% of the nanoparticles in the composition have a cavity size within 50 nm of the average. More preferably at least 60%, 70% or 80% of the nanoparticles have a cavity size within 50 nm of the average. Yet more preferably, at least 50% of the nanoparticles in the composition have a cavity size within 20 nm of the average. More preferably, at least 60%, 70% or 80% of the nanoparticles have a cavity size within 20 nm of the average. Dynamic light scattering may be used to determine the variation in cavity opening size within a composition.

The nanoparticles of the invention may be administered by any suitable route, depending on the nature of the method of treatment, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, intratumoural etc.), transdermally (e.g. by application of a patch, gel or implant) or by inhalation (as a dry powder, a solution, a dispersion, etc).

For example, solid oral forms may contain, together with the nanoparticles of the invention, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Preferably, a composition provided together with a carrier or diluent is a liquid dispersion. Liquid dispersions for oral administration may be syrups, emulsions and suspensions. Suspensions are preferred. The syrups, emulsions and suspensions may contain as carriers, for example, saccharose or saccharose with glycerine and/or mannitol and/or sorbitol. Glucose is a preferred carrier. For example, the nanoparticles may be provided as a suspension in a glucose solution, for example a glucose solution comprising up to 10 wt % glucose, e.g. about 5 wt % glucose.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

An amount of drug-containing nanoparticle to be administered as part of a method of treatment or diagnosis will depend on, for example, the identity and amount of the drug present in the nanoparticles. Thus, the dose of the drug-containing nanoparticle of the invention will typically be equivalent to or less than the dose of the drug present in the nanoparticle if administered alone, i.e. the amount of drug present in the nanoparticles will typically be the same or less than the amount that would be administered if in free form. The dose of the drug-containing nanoparticle of the invention may be less than the equivalent amount of free drug for example to compensate for the enhanced pharmacokinetics seen in the agents of the invention as described above, for example 95% or less, 85% or less, 80% or less, 75% or less, 70% or less, 65% or less, 60% or less, 55% or less, or 50% or less.

In embodiments where the nanoparticles of the invention and another agent are administered separately, the two agents may be administered together in the same pharmaceutical composition or in different compositions intended for separate, simultaneous, concomitant or sequential administration by the same or a different route.

When used alone the amount of the nanoparticle administered can be any appropriate dose as can be determined by a skilled person.

EXAMPLES

The present invention is illustrated below by the following non-limiting examples.

Example 1

Figure 2:
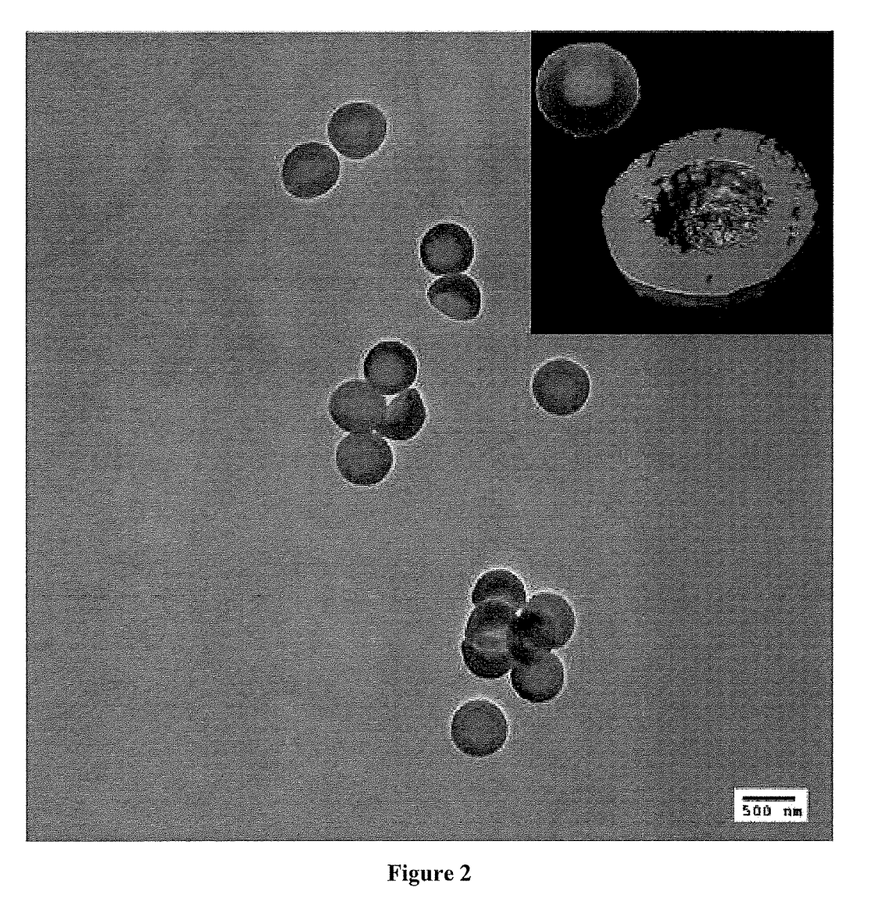
FIG. 2 is a transmission electron micrograph (TEM) of hemispherical nanoparticles produced in Example 1. The inset is a reconstructed 3D model of a hemispherical nanoparticle from a TEM image.
Figure 3:
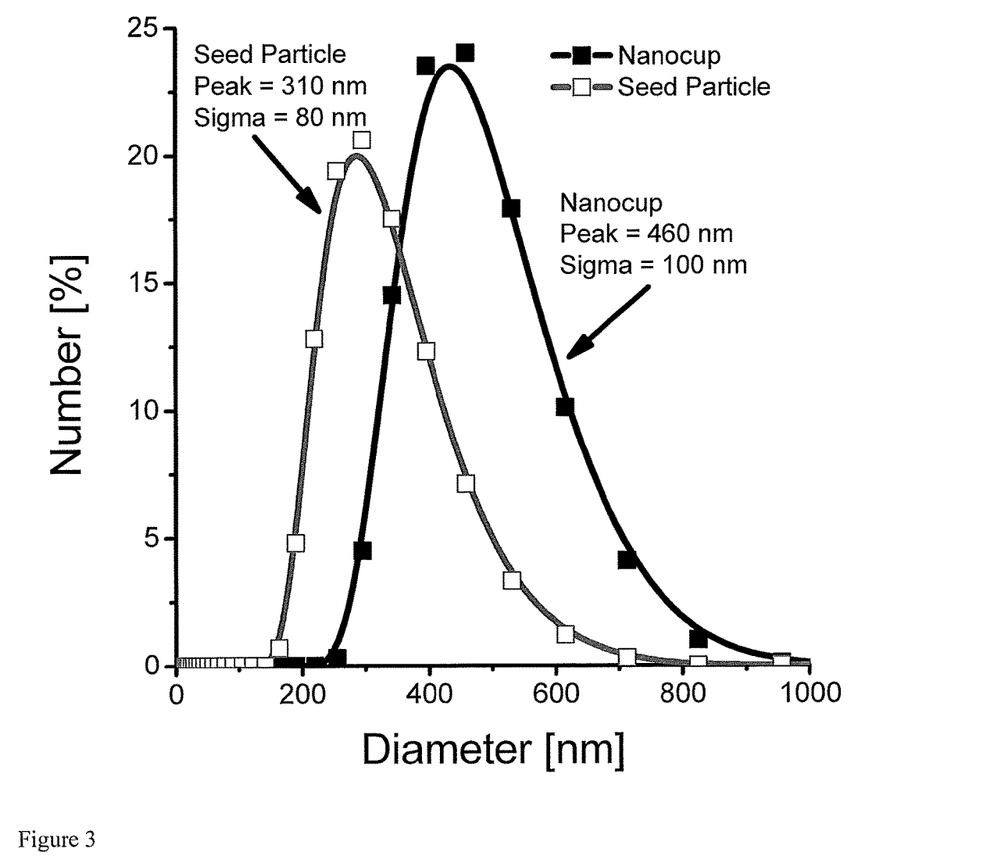
FIG. 3 shows the size distribution of the seed particles used in Example 1 and of the resulting hemispherical nanoparticles produced.
Figure 4:
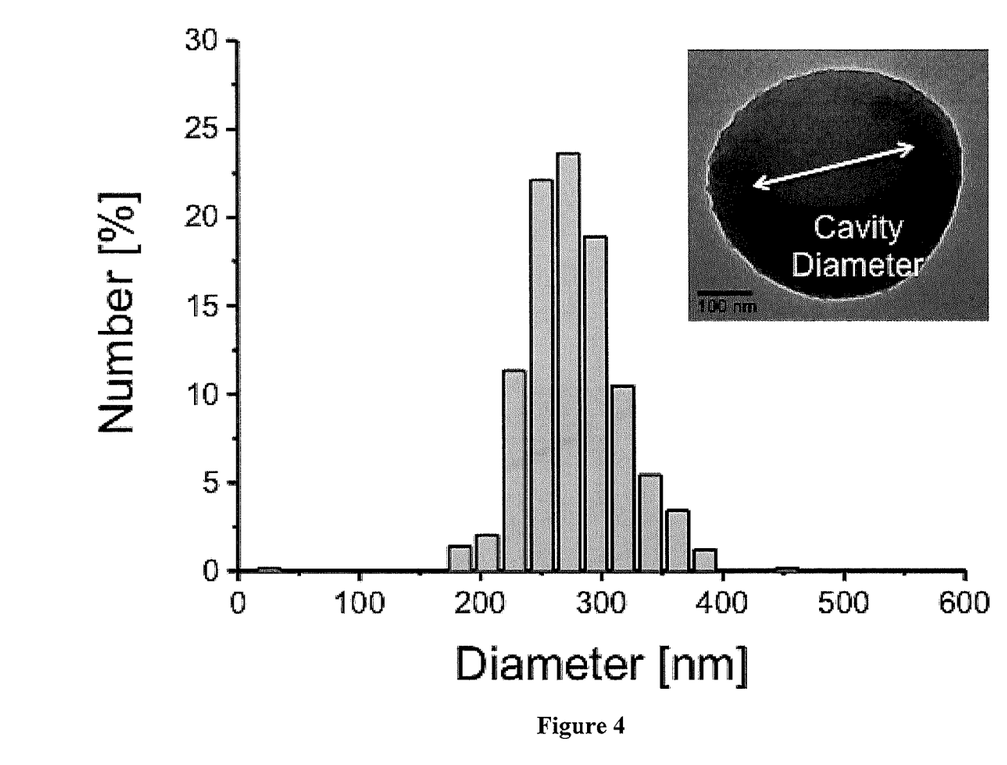
FIG. 4 shows cavity geometry of a hemispherical nanoparticle with a size distribution of measured cavity sizes in a population produced by Example 1.

Nanoparticles having a hemispherical cup, also known as nanocups (NCs), were produced according to the following protocol:

2 ml of 10 wt % 300 nm polystyrene (also known as latex) nanoparticles were mixed with 34 ml of filtered deionised water. The resultant mixture was bubbled with nitrogen gas for 30 minutes in a 100 ml round bottomed flask. The round bottom flask was fitted with a reflux condenser and placed in a water bath at 80° C. The following monomers were added in sequence under stirring: 851 µl MMA, 85 µl HEMA, and 533 µl 80 v/v % DVB. 1.704 ml of 3.5 mg/ml potassium persulfate (KPS) solution was degassed with nitrogen gas. The KPS solution was added. The reaction was maintained for 5 hours, after which time the reaction mixture was washed three times by centrifuging for 30 minutes at 15000 RPM. The resulting nanoparticles, having a hemispherical cup, were suspended in filtered deionised water. TEM and size distribution of the nanocups are shown in FIGS. 2 and 3.

The NC dispersion was placed onto a petri dish and heated to ~40-50° C. overnight. The dish was then placed into a desiccation chamber for 24 hours. The resulting nanoparticles having a hemispherical cup and an air gas pocket were dispersed in filtered deionised water.

Figure 5:
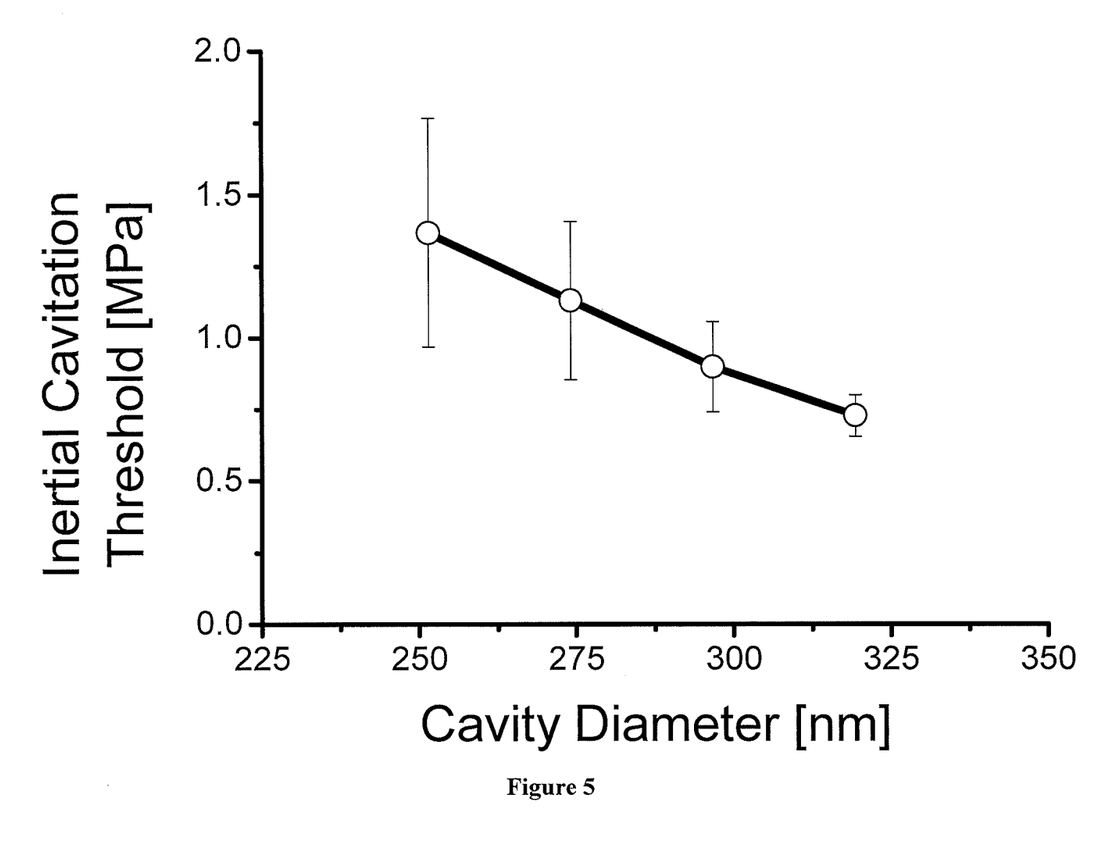
FIG. 5 shows the average inertial cavitation threshold of several batches of the nanoparticles of the invention having different particle and cavity diameters.

FIG. 5 shows the average inertial cavitation threshold of several batches of the nanoparticles of the invention having different particle and cavity diameters. Results were obtained by exposing the nanocups in Example 1 to 200 independent HIFU bursts (0.5 MHz 10-cycle sine wave) at a rate of 20 Hz whilst constrained within a 0.2 mm cylindrical tube. Acoustic emissions were measured with a 15 MHz transducer, also known as a passive cavitation detector. The receiving signal was amplified 25× to reduce RF noise effects, and digitally recorded using a 12-bit DAQ card. The signal was digitally filtered with a 2 MHz high pass filter in order to remove the influence of the driving frequency. Each of the resulting voltage traces was converted to the frequency domain, notch-filtered out harmonics, and inspected for broadband components. If the broadband component (measured as power) for a single pulse was three times greater than that of a tube filled with water, then a cavitation event was said to occur. The probability of inertial cavitation is therefore the percentage of inertial cavitation events out of the 200 transmitted bursts. For a system of a perfectly uniform distribution, the probability of inertial cavitation curve should be a Heaviside function (i.e., a step function ranging from 0 to 100%). However, deviations from the perfect distribution skew the probability curve, giving rise to a linear increase; different cavities within the population will have different cavitation thresholds. Therefore, the individual cavity inertial cavitation thresholds can be deduced by comparing the population of that size in the sample to the probability of inertial cavitation.

Example 2

Nanocups produced in accordance with the protocol of Example 1 were dried and resuspended to provide a gas component within the cavity as follows:

The suspension of nanoparticles in water was air-dried overnight in a large petri dish at 60° C. Next, the dry cake was suspended in a liquid medium (such as DI water or 5% glucose) and rigorously mixed for up to 8 hours to maximise particle dispersion. A combination of 106 µm and 32 µm course filtration was used to remove millimeter-sized agglomerates that did not disperse. Syringe filtration at 2.7 µm and 1.6 µm (Whatman, GE Healthcare Life Sciences, UK) was used to remove micro agglomerates when necessary.

Example 3

Three different sizes of nanocups were produced according to the protocol of Example 1 and dried and resuspended in accordance with Example 2. The variation in size was achieved by use of differing sizes of polystyrene seed nanoparticle as follows:
Small nanoparticles: 100 nm polystyrene seed
Medium nanoparticles: 300 nm polystyrene seed
Large nanoparticles: 460 nm polystyrene seed.

The size distribution of nanocups produced in accordance with Example 1 was determined by dynamic light scattering. The results are depicted in FIG. 7a demonstrating that by variation of the shell size used, nanocups having a small particle size distribution, and having a well-controlled particle size, can be produced.

Figure 7:
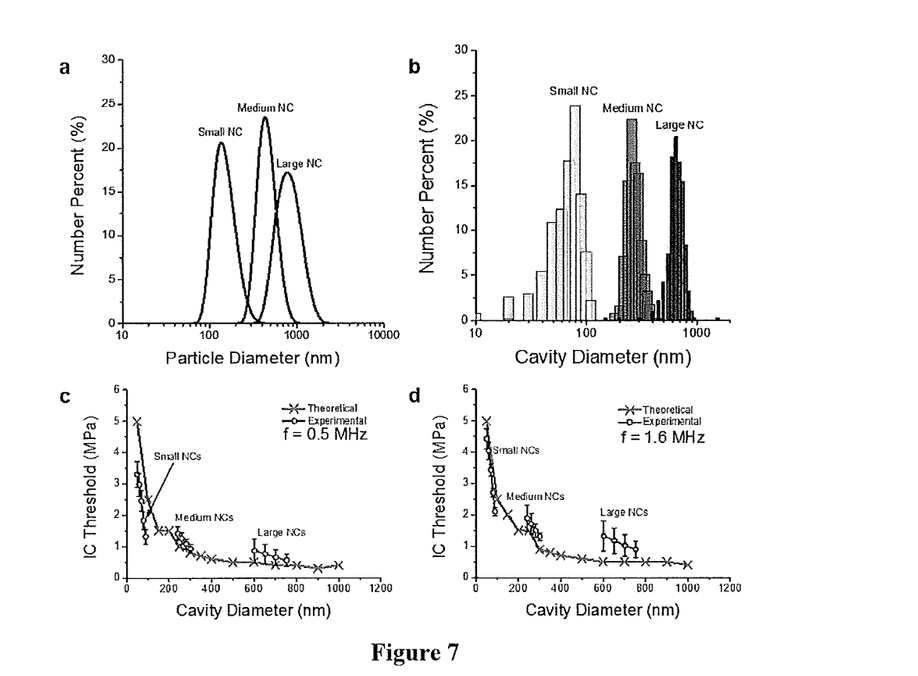

FIG. 7b shows the size distributions of cavity sizes of the small, medium, and large nanocups measured from transmission electron microscopy images. FIGS. 7c and 7d show inertial cavitation thresholds of the small, medium and large nanocups which were determined experimentally and predicted numerically at 0.5 MHz (c) and 1.6 MHz (d).

Experimentally determined inertial cavitation thresholds (open circles) are shown to agree with the inertial cavitation thresholds (grey crosses) predicted by a modified Rayleigh-Plesset model of a hemispherical cavity.

Example 4

A tissue mimic comprised of 1 wt % agarose was exposed to ultrasound for 5 min at 2.2 MPa (5% duty cycle) at 1.6 MHz centre frequency while a fluorescent drug model and fluorescent (9-anthracenylmethyl methacrylate) nanocups prepared using the method of Example 2 were continuously flowing through the channel. The fluorescent drug model used was tetramethylrhodamine—40 kDa Dextran. The tissue mimic was sliced radially to the channel after ultrasound application and the fluorescence image of the drug model visualised. FIG. 8c shows the movement of the drug away from the initial tissue channel following ultrasound exposure. Movement of the drug is mediated by cavitation effects caused by application of ultrasound to the nanocups.

Figure 8:
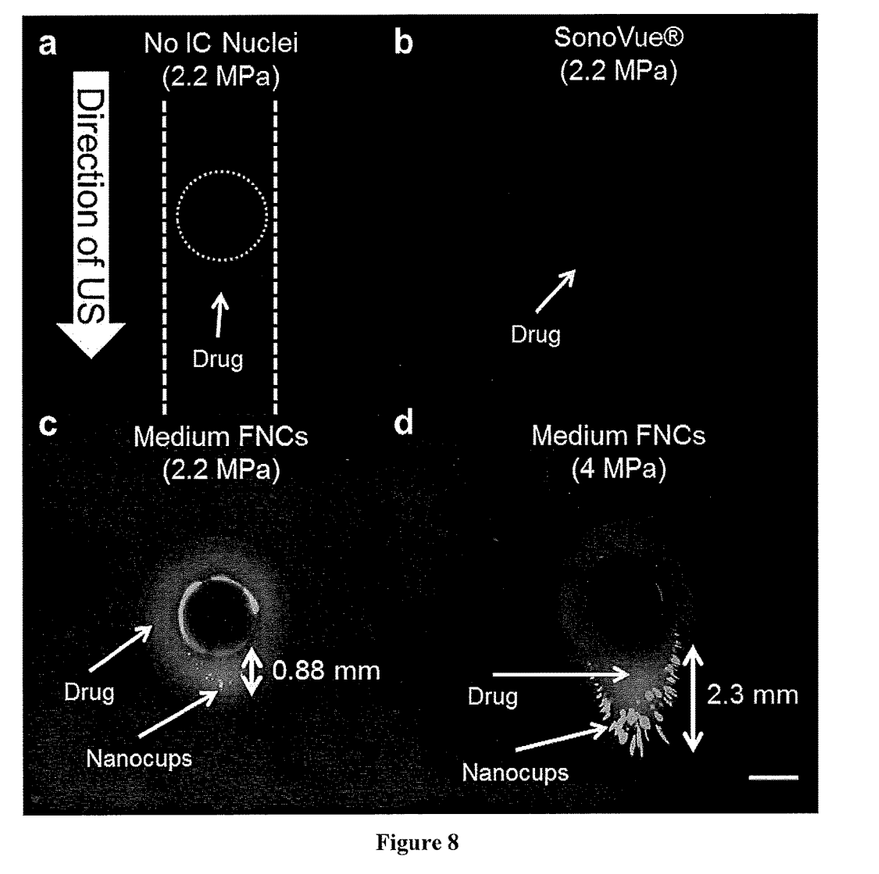
FIG. 8 demonstrates the cavitation effect of the nanocups of the invention, comparing fluorescence images of a fluorescent drug model exposed to ultrasound within a tissue mimic when (a) flowing through the tissue mimic alone, (b) flowing through the tissue mimic with SonoVue® microbubbles, mean diameter 5 micron, available from Bracco and (c) flowing through the tissue mimic with fluorescent nanocups of the invention.

FIG. 8a shows a corresponding example in which the nanocups were omitted and FIG. 8b shows a corresponding example in which the nanocups of the invention are replaced with SonoVue microbubbles (mean diameter 5 microns, available from Bracco). FIG. 8d shows a corresponding example using fluorescent nanocups of the invention which were exposed to ultrasound at 4 MPa at a 1.5% duty cycle and 1.6 MHz centre frequency. In FIG. 8, the white dotted lines indicates the edges of the HIFU focus, and the dotted grey line in (a) represents the edge of the flow vessel. A white arrow demarcates the direction of ultrasound. In all of the images, the model drug and fluorescent nanocups are labeled with arrows in each image. The scale bar represents 1 mm, and is valid for all images.

Example 5

To compare the properties of nanocups which (a) contain a gas pocket in accordance with the invention and (b) which do not contain a gas pocket, two types of nanocups were prepared. Nanocups were prepared in accordance with the protocol of Example 1. Some nanocups were not dried. Others were dried and resuspended in accordance with Example 2.

Figure 9:
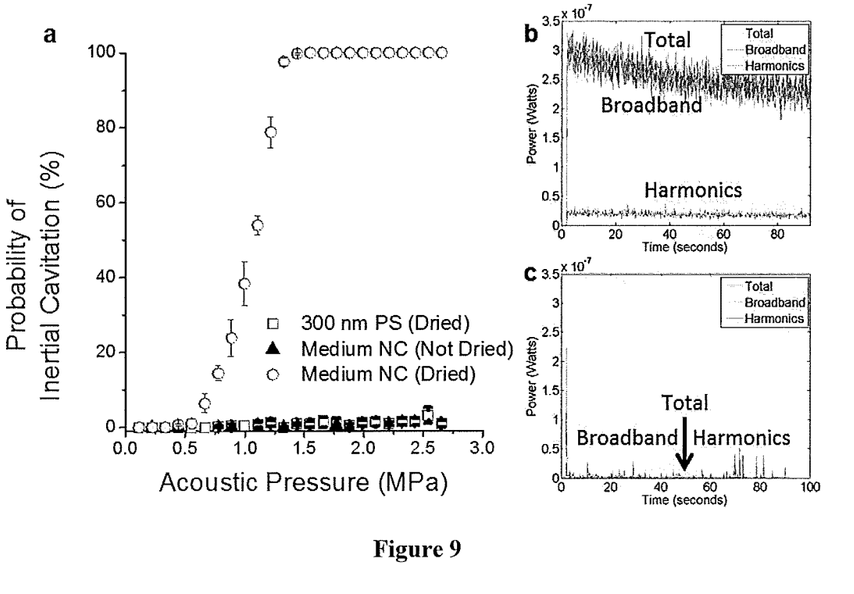
FIG. 9 shows a comparison of cavitation effects achieved using nanocups containing a gas pocket according to the invention, compared with nanocups which have not been dried and resuspended and thus do not contain a gas pocket.

FIG. 9a shows the probability of inertial cavitation of 300 nm polystyrene seed particles that have been dried and resuspended (open squares), nanocups that have not been dried and resuspended (black triangle), and nanocups that have been dried and resuspended (open circles) that have been exposed to ultrasound at 0.5 MHz center frequency.

FIGS. 9b and c show the cavitation power achieved from nanocups above (b) and below (c) the inertial cavitation threshold. The total power has been split into the broadband component (indicative of signals generated by inertial cavitation source) and harmonic component (indicative of signals generated by a stable cavitation source).

Example 6

Luciferin encapsulated within cavitation-sensitive liposomes were formulated by mixing DSPE, cholesterol, DSPC and DSPE-PEG at ratios of 65:25:3:7 (DSPE liposomes) in 2 chloroform: 1 methanol in a round bottomed flask, as described in S. Graham, R. Carlisle, J. Choi, M. Stevenson, A. Shah, R. Myers, K. Fisher, M.-B. Peregrino, L. Seymour, and C. C. Coussios, "Inertial cavitation to non-invasively trigger and monitor intratumoral release of drug from intravenously delivered liposomes," *Journal of Controlled Release*, vol. 178, pp. 101-107, 2014.

Figure 10:
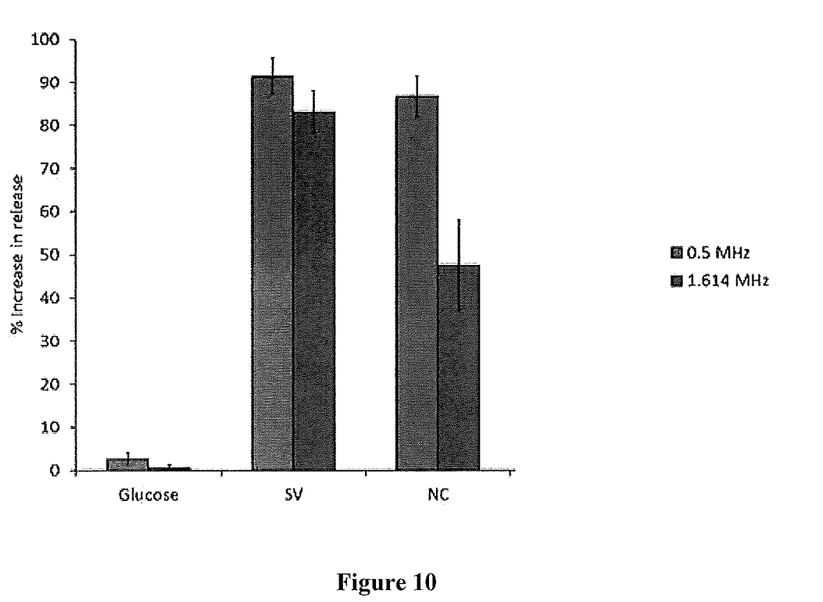
FIG. 10 illustrates the use of nanocups to achieve ultrasound-triggered drug release from cavitation-sensitive liposomes, both at 0.5 MHz and at 1.6 MHz. The release achieved is comparable to that obtained using micron-sized cavitation-inducing agents (Sonovue, Bracco).

Exposure of the liposomes (mean diameter 140 nm) to either 0.5 MHz or 1.6 MHz ultrasound in the presence of glucose alone resulted in no release. Exposure of the liposomes in the presence of Sonovue® (SV) microbubbles (mean diameter 5 microns available from Bracco) resulted in almost complete release at both frequencies. Exposure of the liposomes in the presence of nanocups (NC) (mean diameter 300 nm, produced as described in Examples 1 and 2 above) resulted in equivalent release to SV at 0.5 MHz and slightly inferior release at 1.6 MHz. Results are depicted in FIG. 10.

This demonstrates the feasibility of cavitation-mediated release using cavitation-inducing particles of comparable size to nanoliposomes across the biomedical ultrasound frequency range. Unlike microbubbles, the nanocups can successfully accumulate alongside liposomes within tumours across the leaky tumour vasculature (endothelial junction gap 100-800 nm).

Example 7

Figure 11A:
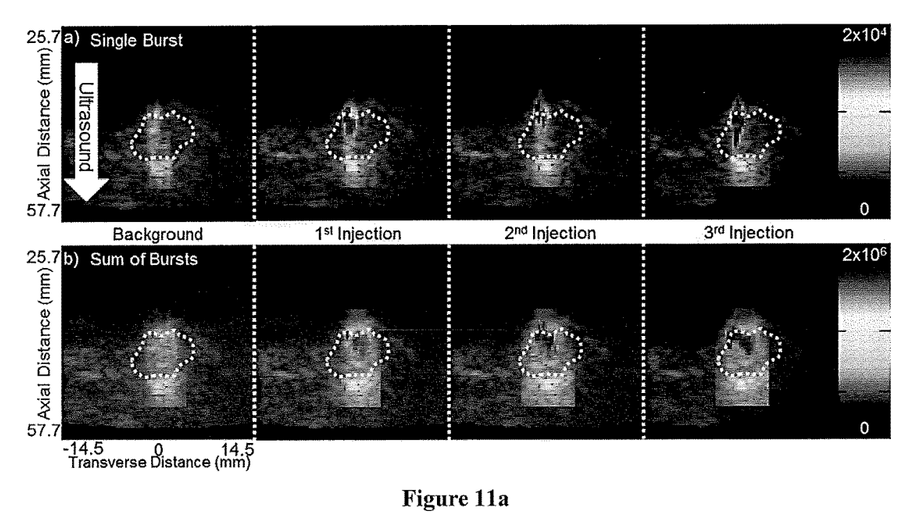
FIG. 11 evidences that nanocups are stable following intravenous administration, enabling cavitation to be initiated in a tumour and mapped in real time using a conventional diagnostic ultrasound system.
Figure 11B:
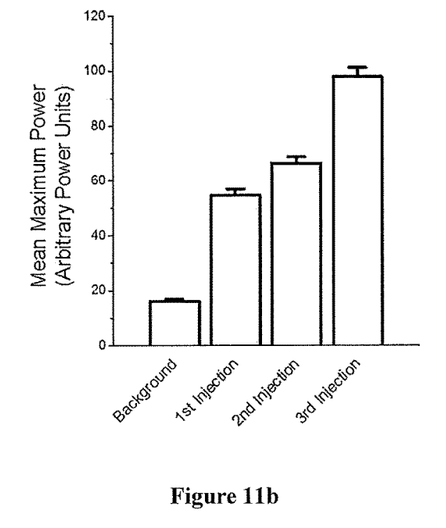

Balb/c mice were subcutaneously implanted with CT-26 murine colorectal cancer cells. Successive intravenous injections of nanocups (NCs) were administered. Cavitation was induced with ultrasound. FIG. 11a depicts the tumour (outlined by dotted line) of volume 100-300 mm$^3$ (as mapped by Passive Acoustic Mapping overlaid onto conventional B-mode images). The top row of FIG. 11a shows mapping of cavitation following a single burst of 2 MHz ultrasound in the tumour, whilst the second row shows cumulative cavitation activity after multiple bursts of ultrasound across the entire tumour. The graph of FIG. 11b evidences increasing levels of cavitation in the tumour following each injection, suggesting that NC successfully accumulate within tumours.

The invention claimed is:

1. A pharmaceutical composition comprising a plurality of polymeric nanoparticles and a pharmaceutically acceptable carrier or diluent which is a liquid medium, wherein each polymeric nanoparticle comprises:
a cup having a cavity, wherein at least a part of the cavity is substantially part-spherical with an opening of at least 50 nm, and
a gas pocket present in the cavity,
wherein the gas pocket is partially encapsulated by the cup, and wherein the polymeric nanoparticle comprises a single cup having a gas pocket present therein.

2. A pharmaceutical composition according to claim 1 wherein the cup is substantially part-spherical.

3. A pharmaceutical composition according to claim 2 wherein the cup is substantially hemi-spherical.

4. A pharmaceutical composition according to claim 1 wherein the cup has a substantially uniform wall thickness.

5. A pharmaceutical composition according to claim 4 wherein the cup has a wall thickness of 10 to 100 nm.

6. A pharmaceutical composition according to claim 5 wherein the cup has a wall thickness of 30 to 70 nm.

7. A pharmaceutical composition according to claim 1 wherein the opening of the cavity is from 50 to 900 nm.

8. A pharmaceutical composition according to claim 7 wherein the opening of the cavity is from 50 to 400 nm.

9. A pharmaceutical composition according to claim 8 wherein the polymeric nanoparticle is from 60 to 500 nm in size.

10. A pharmaceutical composition according to claim 1 wherein both the cup and the cavity are substantially part spherical, the cup has a substantially uniform wall thickness of from 10 to 100 nm and the opening of the cavity has a diameter of from 50 to 900 nm.

11. A pharmaceutical composition according to claim 10 wherein the opening of the cavity is from 50 to 400 nm in size.

12. A pharmaceutical composition according to claim 1 wherein the cup has a depth of greater than 50 nm.

13. A pharmaceutical composition according to claim 1, wherein the polymer is made up of two or more different monomer units, one monomer unit predominantly being present at the inner surface of the cup and another monomer unit predominantly being present at the exterior surface of the cup.

14. A pharmaceutical composition according to claim 1 wherein the polymer is a co-polymer of methyl methacrylate (MMA) and 2-hydroxyethyl methacrylate (HEMA).

15. A pharmaceutical composition according to claim 14 wherein the polymer is obtainable by using divinylbenzene as a crosslinking agent in a free-radical polymerization reaction.

16. A pharmaceutical composition according to claim 1 wherein the polymer is a crosslinked polymer.

17. A pharmaceutical composition according to claim 1 wherein the polymeric nanoparticle comprises one or more release agents.

18. A pharmaceutical composition according to claim 17 wherein a release agent is present within the cup, on an exterior surface of the cup and/or in the cavity of the cup.

19. A pharmaceutical composition according to claim 18 wherein the polymeric nanoparticle comprises a first release agent in the cavity of the cup, and a second release agent on an exterior surface of the cup.

20. A pharmaceutical composition according to claim 17 wherein one or more release agents is a drug.

21. A composition according to claim 1, wherein the composition comprises polymeric nanoparticles having a polydispersity index of no more than 0.2.

22. A method of producing a polymeric nanoparticle comprising:
a cup having a cavity, wherein at least a part of the cavity is substantially part-spherical with an opening of at least 50 nm, and
a gas pocket present in the cavity,
wherein the gas pocket is partially encapsulated by the cup, and wherein the polymeric nanoparticle comprises a single cup having a gas pocket present therein, which method comprises:
providing a seed particle;
partially coating the seed particle, by carrying out polymerization on the surface of the seed particle to provide a polymer coating, wherein the polymer induces swelling and deformation to provide a cup having the cavity;
drying the cup;
providing gas to the cup to produce a pocket of the gas within the cavity; and
resuspending the polymeric nanoparticle in a liquid medium.

23. A method according to claim 22, wherein the steps of drying and providing gas to the cup are carried out by drying the cup in air.

24. A method according to claim 22, wherein the seed particle is coated by carrying out emulsion polymerization in the presence of the seed particle, the polymerization being carried out using one or more monomers and/or pre-polymers and optionally a cross-linking agent.

25. A method according to claim 24 wherein the cross-linking agent is divinylbenzene.

26. A method according to claim 25, wherein the polymerization is a free-radical polymerization.

27. A method according to claim 22, wherein the seed particle has a diameter of from 100 to 600 nm.

28. A method according to claim 22, wherein the polymeric nanoparticle comprises one or more release agents, and the method further comprises providing a release agent (a) as a coating on the seed particle; and/or (b) during polymerization; and/or (c) to the exterior surface of the cup.

29. A method according to claim 28, wherein two or more different release agents are provided.

30. A method of treatment or diagnosis of a human or animal subject, wherein the method comprises administering to the subject a pharmaceutical composition comprising a plurality of polymeric nanoparticles, each polymeric nanoparticle comprising:
a cup having a cavity, wherein at least a part of the cavity is substantially part-spherical with an opening of at least 50 nm, and
a gas pocket present in the cavity,
wherein the gas pocket is partially encapsulated by the cup, wherein the polymeric nanoparticle comprises a single cup having a gas pocket present therein, and wherein the pharmaceutical composition further comprises a pharmaceutically acceptable carrier or diluent which is a liquid medium; and exposing the subject to ultrasound.

31. The method of claim 30, wherein the ultrasound has a pressure amplitude of less than 5 MPa.

32. The method of claim 30, wherein the method is for the treatment or diagnosis of a tumor.

33. The method of claim 30, wherein the polymeric nanoparticle comprises one or more release agents, wherein the one or more release agents is a drug, and wherein the drug is released from the polymeric nanoparticle upon exposure to ultrasound.

34. The method of claim 30, wherein the polymeric nanoparticle comprises a first release agent in the cavity of the cup, and a second release agent on an exterior surface of the cup, and wherein the first and second release agents mix upon exposure of the polymeric nanoparticle to ultrasound.

\* \* \* \* \*